(12) United States Patent
Bainbridge

(10) Patent No.: US 8,206,363 B2
(45) Date of Patent: Jun. 26, 2012

(54) MEDICAL SLEEVE

(75) Inventor: Lionel Christopher Bainbridge, Derbyshire (GB)

(73) Assignee: Derby Hospitals NHS Foundation Trust, Derbyshire (GB)

( * ) Notice: Subject to any disclaimer, the term of this patent is extended or adjusted under 35 U.S.C. 154(b) by 949 days.

(21) Appl. No.: 10/598,144

(22) PCT Filed: Feb. 17, 2005

(86) PCT No.: PCT/GB2005/000561
§ 371 (c)(1),
(2), (4) Date: Aug. 27, 2008

(87) PCT Pub. No.: WO2005/079691
PCT Pub. Date: Sep. 1, 2005

(65) Prior Publication Data
US 2011/0125112 A1    May 26, 2011

(30) Foreign Application Priority Data

Feb. 18, 2004  (GB) .................................. 0403648.9

(51) Int. Cl.
*A61F 13/00*  (2006.01)
(52) U.S. Cl. ........ 604/304; 604/293; 604/303; 604/308; 604/356; 604/357
(58) Field of Classification Search .................. 604/293, 604/303, 308, 356, 357, 304
See application file for complete search history.

(56) References Cited

U.S. PATENT DOCUMENTS

| | | | | | |
|---|---|---|---|---|---|
| 3,186,404 | A | * | 6/1965 | Gardner | 602/13 |
| 3,327,705 | A | * | 6/1967 | Spira et al. | 602/48 |
| 3,744,491 | A | * | 7/1973 | Fischer | 604/23 |
| 3,968,792 | A | * | 7/1976 | Small | 128/856 |
| 4,991,593 | A | * | 2/1991 | LeVahn | 128/856 |
| 5,029,579 | A | * | 7/1991 | Trammell | 128/205.26 |
| 5,063,919 | A | | 11/1991 | Silverberg | 128/82 |
| 5,312,385 | A | * | 5/1994 | Greco | 604/356 |
| 5,437,602 | A | * | 8/1995 | Polyakov et al. | 600/21 |
| 5,447,504 | A | * | 9/1995 | Baker et al. | 604/289 |
| 5,494,050 | A | * | 2/1996 | Reyes | 128/849 |
| 5,592,953 | A | | 1/1997 | Delao | |
| 5,848,998 | A | * | 12/1998 | Marasco, Jr. | 604/290 |

(Continued)

FOREIGN PATENT DOCUMENTS

DE     29913123     3/2000

(Continued)

OTHER PUBLICATIONS

UK Search Report for corresponding Application No. GB 0 403 648.9 dated Aug. 26, 2004.

*Primary Examiner* — Tatyana Zalukaeva
*Assistant Examiner* — Ginger T Chapman
(74) *Attorney, Agent, or Firm* — Renner, Otto, Boisselle & Sklar, LLP

(57) ABSTRACT

The invention provides a device adapted to assist the sterilization of a limb surface, comprising a flexible tubular sleeve, closed at one end, shaped and sized so as to loosely fit, in use, around the limb of a patient whose limb surface is to be sterilized. The sleeve bas limb-sealing means, located close to or at each end of the sleeve, and each capable of forming, in use, a seal between the sleeve and the limb of a patient. The device is particularly suitable to assist in de-contamination of limbs prior to surgery thereon.

14 Claims, 5 Drawing Sheets

U.S. PATENT DOCUMENTS

| | | |
|---|---|---|
| 6,276,364 B1 | 8/2001 | Warner |
| 6,635,035 B1 * | 10/2003 | Marasco et al. ............. 604/290 |
| 2004/0171998 A1 * | 9/2004 | Marasco, Jr. ................ 604/290 |
| 2006/0291755 A1 * | 12/2006 | Olin et al. ..................... 383/66 |
| 2008/0119801 A1 * | 5/2008 | Moore ........................ 604/306 |
| 2008/0168995 A1 * | 7/2008 | Yardan et al. ................ 128/854 |

FOREIGN PATENT DOCUMENTS

| | | |
|---|---|---|
| DE | 200 02 902 | 4/2000 |
| GB | 2276323 | 9/1994 |
| NL | 8 102 851 | 1/1983 |
| WO | 03/090598 | 11/2003 |

* cited by examiner

MEDICAL SLEEVE

This application is a national phase of International Application No. PCT/GB2005/000561 filed Feb. 17, 2005 and published in the English language.

FIELD OF THE INVENTION

The invention relates to a device to assist the application of preparations such as antimicrobial agents, medicaments and cosmetics to the surface of a user's limb. The device is particularly suitable to assist in decontamination of limbs prior to surgery thereon.

BACKGROUND TO THE INVENTION AND PRIOR ART KNOWN TO THE APPLICANT

The decontamination and sterilisation of skin is one of the most important parts of any surgical operation. Since the work of Pasteur, Lister, Semmelweiss and others, we have known that bacteria cause infection. As a consequence of their work, a variety of methods are now routinely used to reduce the bacterial count on the surface of the skin prior to surgical procedures.

Standard techniques employed to this end include: skin depilation (i.e. removal of hair) immediately prior to surgery; removal of any visible contamination; washing of the skin with soap and water; painting of the skin with an anti-microbial agent.

This last part of the preparation before surgery (i.e. the use of an anti-microbial agent) is often known amongst surgeons as the 'skin prep'. It is this procedure that has turned surgery from a life-threatening procedure into the safe procedure it is today. Prior to the introduction of skin prep, mortality rates from wound infection could be as high as 40%. Following the introduction of skin preparation, the infection rate from bacteria residing on the skin has fallen to almost unrecordable levels.

However, the introduction of more complex surgery, and especially joint-replacement surgery, where the presence of foreign material in the body potentiates the infection, has led to a reassessment of skin preparation.

It is known that anti-microbial agents such as iodine, chlorhexidine and alcohol need time in contact with the skin to kill the bacteria. It is also known that there is a reservoir of skin-associated organisms that reside in the sweat glands and hair follicles of the body. Therefore, a skin preparation agent that stays on the skin for a period of time prior to surgery will be more effective in reducing the bacterial count. Furthermore, if the agent forms a film on the skin which is retained throughout the operation, then this is also of benefit.

A common technique for application of the anti-microbial agent is as follows: the surgeon or the surgeon's assistant is supplied with a bowl containing the skin preparation fluid, and something for applying the agent. This usually comprises a swab or a piece of sponge held in a pair of locking forceps. For preparation of the abdomen or chest, this is usually excellent. The area to be cleaned is roughly flat, does not need to be moved, and is clearly visible to the surgeon.

For structures such as the arm and leg, the situation is more difficult. As the skin prep is carried out after anaesthesia has commenced, the limb must be held in the air by an assistant. It is not possible to clearly see the entire surface of limb. In particular, toes and fingers are difficult to prepare. The person who holds the limb is 'non-sterile'—i.e. has not been through the de-contamination procedures carried out by surgeons and their assistants—and so has to transfer the support of the limb to the sterile surgical team. This whole procedure takes a significant amount of time and can be prone to contamination. If a tourniquet is being used, then the anti-microbial agent can seep under the tourniquet and cause contact burns.

Whilst lifting of an arm is not too difficult, lower limbs have considerable weight and may have to be supported whilst the limb is cleaned. As a result, the non-sterile member of the team initially supporting the limb may have to support it at arm's length to allow the surgical team access to the limb. This can be dangerous, not only for the patient, if the leg is dropped, but also to the person holding the limb, and can result in back strain and other similar injuries.

Whilst these problems, and the solutions provided by the current invention, are described in terms of human surgical procedures, they clearly have parallels in the veterinary field.

Furthermore, whilst the invention relates primarily to problems associated with the application of anti-microbial agents to limbs, there are similar problems in associated areas for which the invention has considerable application. For example, it is often required to apply other agents such as medicaments, depilants (hair-removal agents) and cosmetic preparations such as artificial tanning solutions to limbs of users, without undue contact of the agent with the hand of the person applying it. Furthermore, these agents may need to be left in contact with the skin for some length of time without the agent drying or coming into contact with, for example, clothes, furniture or other parts of the body. The invention also has application as temporary wound-dressing, for example in the treatment of burns, and allows wound inspection following surgery or during ward rounds. Prior art known to the applicant comprises former patent applications GB 2276323, WO 03/090598, DE 29913123U1 and, U.S. Pat. No. 6,276,364 and U.S. Pat. No. 5,592,953

It is an object of the present invention to attempt a solution to these problems.

SUMMARY OF THE INVENTION

The invention provides a device adapted to assist the sterilisation of a limb surface, and comprising: a flexible tubular sleeve, closed at one end, shaped and sized so as to loosely fit, in use, around the limb of a patient whose limb surface is to be sterilised; and respective limb-sealing means, each located close to or at a respective end of said sleeve, and each capable of forming, in use, a seal between the sleeve and the limb of a patient.

Preferably, at least one of the limb-sealing means comprises a perforated, elastic diaphragm. This type of limb-sealing means has a particular advantage over eg. a simple drawstring arrangement or elasticated cuff in that the elastic diaphragm can stretch to accommodate the varying diameters of a patient's limb without either the need to adjust the drawstring, or the possibility of an ineffective seal between an elasticated cuff and a patient's limb.

In any embodiment of the invention it is also preferable that at least one of the limb-sealing means comprises a substantially frustoconical portion. Not only can this arrangement assist in the insertion of a patient's limb into the limb-sealing means, but it may also be used to position the limb-sealing means, before use, away from contamination.

In any aspect of the invention, the limb-sealing means are preferably constructed so as to create a wiping action when slid, in use, along a patient's limb. This feature is particularly advantageous as it serves to remove any excess fluid that has been applied to a patient's limb before the commencement of surgery.

In any aspect of the invention, both ends of the said sleeve are advantageously initially closed. By closing both ends of the sleeve, it is possible to produce the device in a sterile fashion and to maintain that sterility during storage. Additionally the sleeve may be provided as part of a sterile pack.

In any aspect of the invention, the sleeve of the device is preferably substantially transparent. By this means, it is possible for an operator or a user to see the limb whilst applying fluid such as an anti-microbial formulation. This enables the user to ensure that the fluid is spread evenly over the limb and reaches all exposed parts, such as between the fingers and toes.

In any aspect of the invention, it is preferable that at least one of any sealed end of the sleeve is perforated, nicked, weakened or otherwise adapted to assist opening of that sealed end. In the surgical context, it is advantageous to be able to open an end of the sleeve quickly and without use of cutting means such as scissors or a scalpel. This avoids risk of injury to the patient and contamination of surgical or other instruments.

In any aspect of the invention, it is advantageous that the device further comprises at least one tab or loop to assist pulling the sleeve, in use, along a patient's limb. When used in the field of pre-surgical limb sterilisation, it is important not to re-introduce any contamination onto the patient's limb following the 'skin prep'. By providing tabs or loops, especially at the end closest to the extremity of the limb, a surgeon or surgeon's assistant can pull the sleeve along the limb and avoiding contact with the sterilised skin surface. As well as flexible tabs or loops, such a loop could advantageously comprise a rigid ring, large enough to pass over a patient's limb, to facilitate pulling the sleeve along the limb. Such means to assist pulling the sleeve may be advantageously located at either or both ends of the sleeve to assist the two pulling actions envisaged: firstly to pull a first end over the limb to enclose it; and secondly to pull the send end up to meet the first end, thereby exposing the treated skin.

In any aspect of the invention, it is advantageous for the device to further comprise fastening means to hold the two ends of the sleeve close together whilst the sleeve is positioned on a patient's limb. In use, and as illustrated and described below, the two ends of the sleeve may be brought together on a patient's limb causing the sleeve to adopt a bunched configuration. Provision of fastening means, such as adhesive tape, a stud type fastening or even a simple tie fastening allows the operator to maintain the sleeve in that configuration without it slipping back down the patient's limb.

In any aspect of the invention, it is preferable that the device has an easily rupturable container of sterilising agent inside (in use) the sleeve. It is particularly advantageous to provide such a container within the sleeve as it will remove the need for an operator to have contact with the sterilising agent (or other medicament or cosmetic preparation) during the application process. Furthermore, this allows a pre-metered dose of sterilising agent to be provided thus ensuring that sufficient material is used.

In any aspect of the invention, it is advantageous that the sleeve further comprises a valve arrangement to allow egress of air from within the sleeve whilst the sleeve is positioned on a patient's limb. In one such aspect, the valve would be a one-way valve, to allow air to escape from between the patient's limb and the sleeve, in use, so facilitating e.g. moving both ends of the sleeve to a common point on the limb (to expose the skin surface) without the sleeve "ballooning" due to trapped air. In another such aspect, the valve arrangement would comprise a simple tap arrangement to allow air to escape from, or to be introduced into the sleeve. For situations requiring aseptic conditions, the valve arrangement may be provided with a air filter suitable for removing airborne contaminants such as bacteria. In this arrangement, therefore, the sleeve may be inflated or deflated at will. In this way, the relative proximity of the sleeve and the patient's skin may be controlled: by inflating the sleeve, it is held away from the skin, allowing improved inspection of e.g. wounds; by deflating the sleeve, it may be repositioned more easily, and may be used to apply pressure to the patient's limb, or to dressings or medicaments applied thereon.

Preferably a limb sealing means is provided which is sized and shaped to be extendable beyond an opening formed by removal of the sealed end of the device.

Preferably at least one of the limb sealing means adapts to fit limbs of differing circumference without the need to cut sections from the device.

Preferably a resealable portal is provided.

In a second broad aspect, the invention provides a device adapted to assist the sterilisation of a limb surface, and comprising:
a flexible tubular sleeve, closed at one end, shaped and sized so as to loosely fit, in use around the limb of a patient whose limb surface is to be sterilised; and respective limb-sealing means, each located close to or at a respective end of said sleeve, and each capable of forming, in use, a seal between the sleeve and the limb of a patient and incorporating a perforated elastic diaphragm.

In a third broad aspect, the invention provides a device adapted to assist the sterilisation of a limb surface, and comprising:
a flexible tubular sleeve, closed at one end, shaped and sized so as to loosely fit, in use around the limb of a patient whose limb surface is to be sterilised;
and respective limb-sealing means, each located close to or at a respective end of said sleeve, and each capable of forming, in use, a seal between the sleeve and the limb of a patient and wherein the sleeve is substantially transparent.

In a fourth broad aspect, the invention provides a device adapted to assist the sterilisation of a limb surface, and comprising:
a flexible tubular sleeve, closed at one end, shaped and sized so as to loosely fit, in use around the limb of a patient whose limb surface is to be sterilised;
and respective limb-sealing means, each located close to or at a respective end of said sleeve, and each capable of forming, in use, a seal between the sleeve and the limb of a patient and wherein at least one of any sealed end of the sleeve is perforated, nicked, weakened or otherwise adapted to assist opening of that sealed end.

In a fifth broad aspect, the invention provides a device adapted to assist the sterilisation of a limb surface and comprising:
a flexible tubular sleeve, closed at one end, shaped and sized so as to loosely fit, in use around the limb of a patient whose limb surface is to be sterilised;
and respective limb-sealing means, each located close to or at a respective end of said sleeve, and each capable of forming, in use, a seal between the sleeve and the limb of a patient and wherein a valve arrangement is provided to allow egress of air from within the sleeve whilst the sleeve is positioned on a patient's limb.

In a sixth broad aspect, the invention provides a device adapted to assist the sterilisation of a limb surface and comprising:

a flexible tubular sleeve, closed at one end, shaped and sized so as to loosely fit, in use around the limb of a patient whose limb surface is to be sterilised;

and respective limb-sealing means, each located close to or at a respective end of said sleeve, and each capable of forming, in use, a seal between the sleeve and the limb of a patient and a limb sealing means which is sized and shaped to be extendable beyond an opening formed by removal of the sealed end of the device.

In a seventh broad aspect, the invention provides a device adapted to assist the sterilisation of a limb surface and comprising:

a flexible tubular sleeve, closed at one end, shaped and sized so as to loosely fit, in use around the limb of a patient whose limb surface is to be sterilised;

and respective limb-sealing means, each located close to or at a respective end of said sleeve, and each capable of forming, in use, a seal between the sleeve and the limb of a patient and wherein at least one of the limb sealing means adapts to fit limbs of differing circumference without the need to cut sections from the device.

In an eighth broad aspect, the invention provides a device adapted to assist the sterilisation of a limb surface and comprising:

a flexible tubular sleeve, closed at one end, shaped and sized so as to loosely fit, in use around the limb of a patient whose limb surface is to be sterilised;

and respective limb-sealing means, each located close to or at a respective end of said sleeve, and each capable of forming, in use, a seal between the sleeve and the limb of a patient and wherein a re-sealable portal is provided.

Included within the scope of the invention is a device substantially as described herein with reference to and as illustrated by any appropriate combination of the accompanying drawings.

BRIEF DESCRIPTION OF THE DRAWINGS

The invention will be described with reference to the accompanying drawings in which.

EMBODIMENTS OF THE INVENTION

Figure 1:
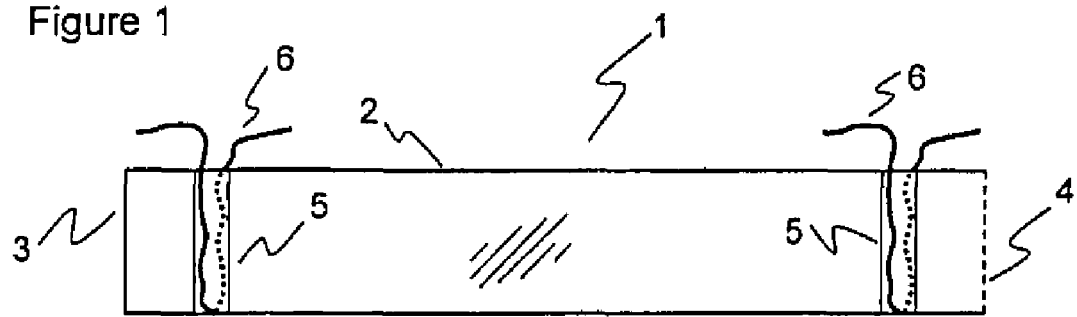
FIG. 1 is a schematic plan view of the device.

FIG. 1 is a schematic plan of the device, shown generally as 1, comprising a flexible tubular sleeve 2 made of a flexible, transparent, plastics material. The sleeve is closed at one end 3 and open at the other end 4. Close to each end of the sleeve there is a limb-sealing means comprising a drawstring 6 located within a channel 5, which surrounds the sleeve 2. The sleeve 2 fits loosely around the limb of a patient and each of the limb-sealing means may be operated by means of the drawstrings 6 to form a seal, in use, between the sleeve 2 and the limb of a patient.

Figure 2:
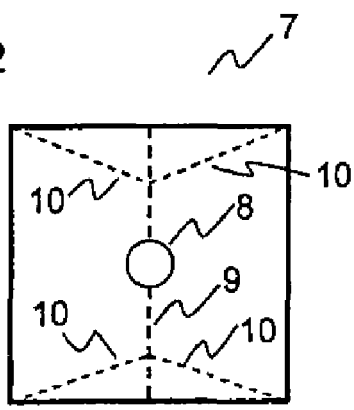
FIG. 2 and FIG. 3 are schematic diagrams illustrating the construction of a frustoconical, perforated, elastic diaphragm suitable for use as a limb-sealing means.
Figure 3:
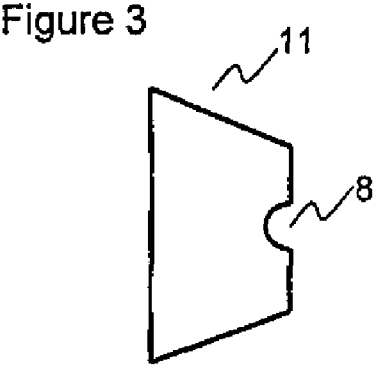

FIGS. 2 and 3 illustrate a design for an embodiment of the limb-sealing means, comprising a perforated, elastic diaphragm. FIG. 2 illustrates a sheet of elastic material 7, such as rubber, which has a perforation/hole 8 in the centre. The dashed line 9 indicates where to fold the sheet 7, and the dashed lines 10 illustrate where to subsequently seal and trim the sheet 7. FIG. 3 illustrates a plan view of the folded, sealed and trimmed sheet 7 forming a frustoconical limb-sealing means, generally indicated as 11, with a hole 8.

Figure 4:
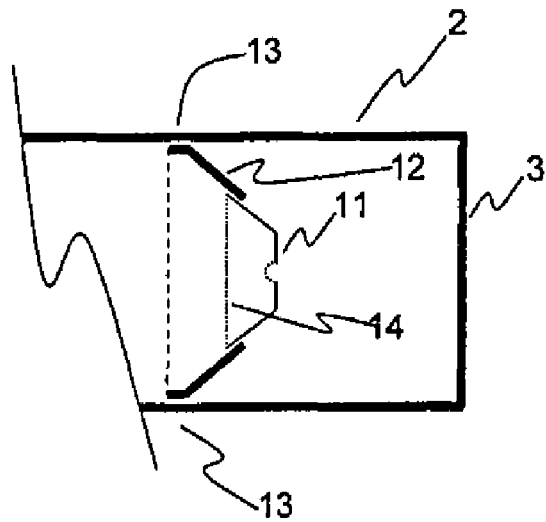
FIG. 4 is a schematic diagram illustrating the insertion of a limb-sealing means within a sleeve.

FIG. 4 illustrates a way in which a limb-sealing means may be incorporated into a sleeve. There is illustrated, in part, a sleeve 2 with a sealed end 3. Such a sleeve may conveniently be manufactured from a heat-sealable plastics material. Located within the sleeve is a frustoconical member 12 of a similar plastics material that may be heat-sealed to the sleeve around its periphery, indicated generally by 13. At the smaller end of this member 12 is located a limb-sealing means 11 (as illustrated in FIG. 3) which may be sealed to the frustoconical member 12 where they meet, generally indicated by 14.

Figure 5:
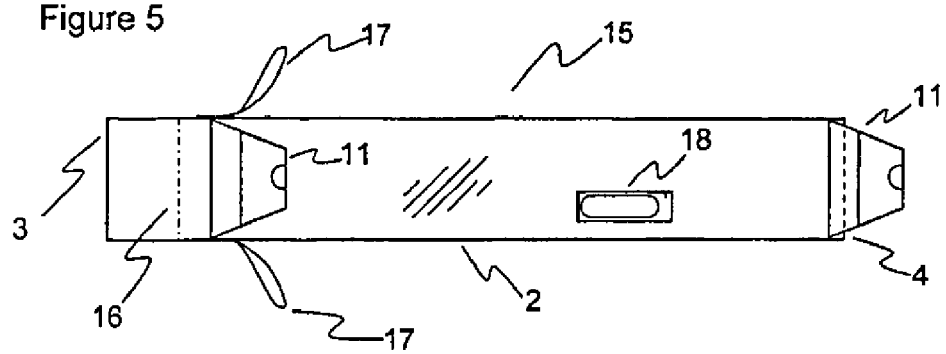
FIG. 5 is a schematic diagram of an embodiment of the invention incorporating frustoconical limb-sealing means, loops to assist pulling of the sleeve and a container of sterilising fluid.

FIG. 5 illustrates another, preferred, embodiment of the invention, generally indicated as 15. The device comprises a flexible, transparent sleeve 2 with a closed end 3 and an open end 4. Located at the open end 4 is a limb-sealing means 11 of the frustoconical, elastic diaphragm type as discussed above. A second limb-sealing means 11 is located toward the sealed end 3 of the sleeve 2. The sealed end 3 is weakened, by perforation 16, to assist opening of the sealed end 3. The device further comprises loops 17 attached to the sleeve 2 and close to the initially sealed end 3.

Figure 6:
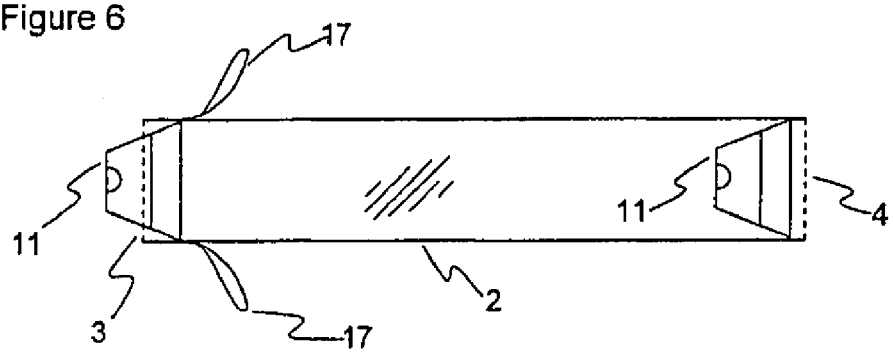
FIG. 6 illustrates the embodiment of FIG. 5 with the limb-sealing means everted.

FIG. 6 illustrates the embodiment of FIG. 5 in which the frustoconical limb-sealing means 11 are shown in their everted configuration, after having opened the initially sealed end 3 and pulled the sleeve 2 over the limb of a patient (not shown) in a left to right direction in the illustration.

Figure 7:
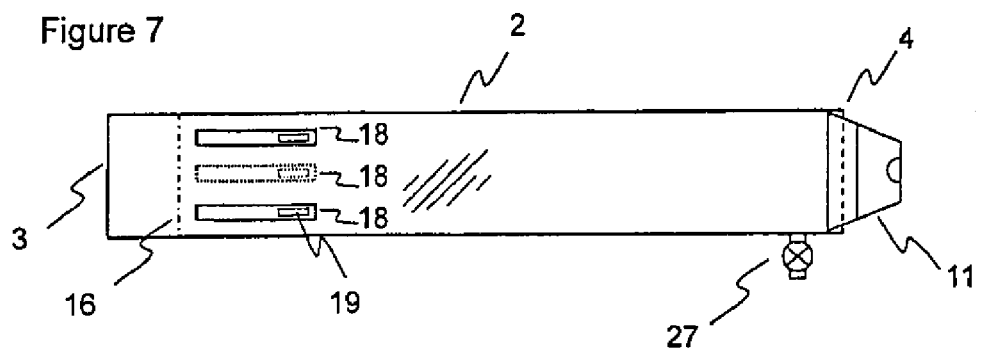
FIG. 7 illustrates an embodiment of the invention with fastening means.

FIG. 7 illustrates an embodiment of the invention further comprising fastening means 18 attached to the sleeve 2. In this embodiment, the fastening means 18 comprise self-adhesive tags, attached to the sleeve 2, each having a peel-off protective strip 19 over the adhesive. In this embodiment, three such tags are provided. The second limb-sealing means of this embodiment is not illustrated in FIG. 7 for sake of clarity. Also illustrated in FIG. 7 is a valve arrangement 27 to allow control of air movement in and out of the sleeve when it is positioned on a patient's limb.

Use of the Device

FIGS. 8 to 12 illustrate an embodiment of the device in use on the arm of a patient.

Figure 8:
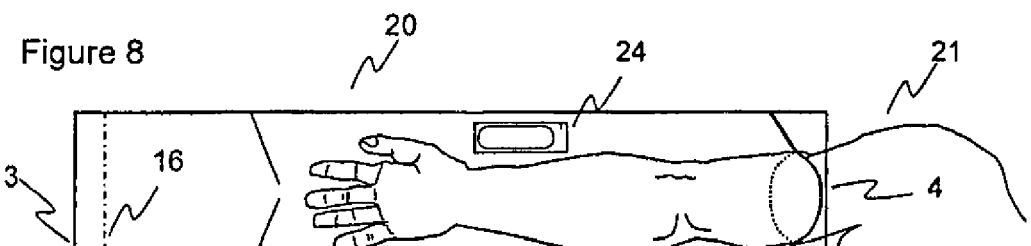
FIGS. 8 to 12 illustrate an embodiment of the invention in use, on a patient's arm.

FIG. 8 illustrates an embodiment of the device 20 in position around the arm 21 of a patient. The arm passes through the first limb-sealing means 22 into the interior of the sleeve 2. The second limb-sealing means 23 is, at this stage, not surrounding the arm 21. Within the sleeve 2 is located a sachet of skin-sterilisation fluid 24.

Figure 9:
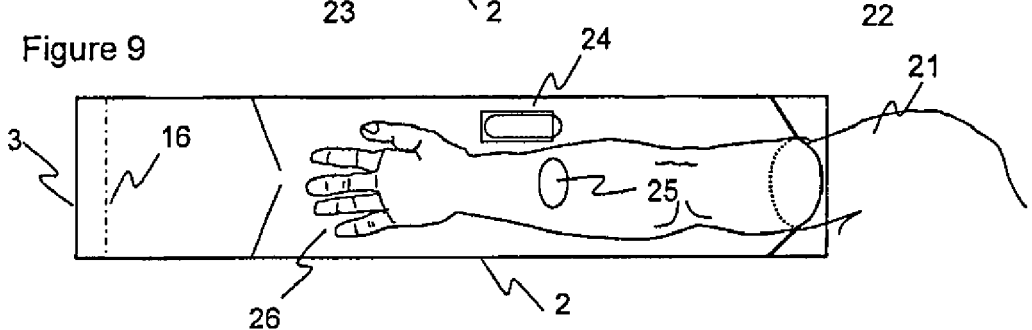

In FIG. 9, the sachet 24 has been opened to release its contents 25 which now be spread over the surface of the arm 21. This process may be carried out by, or with the assistance of the patient, or by the surgeon's assistant alone. The transparent nature of the sleeve 2 enables the fluid to be seen and helps to ensure that it is spread over the entire surface, especially between the fingers 26.

Figure 10:
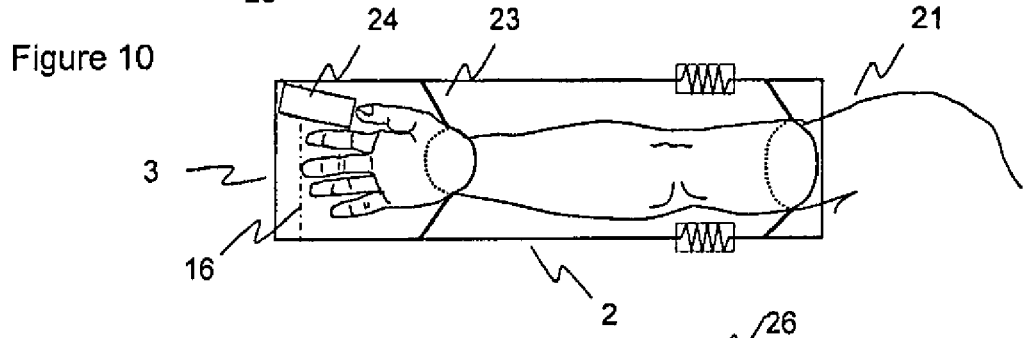

FIG. 10 illustrates the stage where the arm of the patient 21 has been pushed through the second sealing means 23 into the space between that sealing means 23 and the sealed end 3 of the sleeve 2. The spent sachet 24 of sterilising fluid has also been passed into this section of the sleeve 2 ready for disposal.

The patient may conveniently be anaesthetised at this stage.

Figure 11:
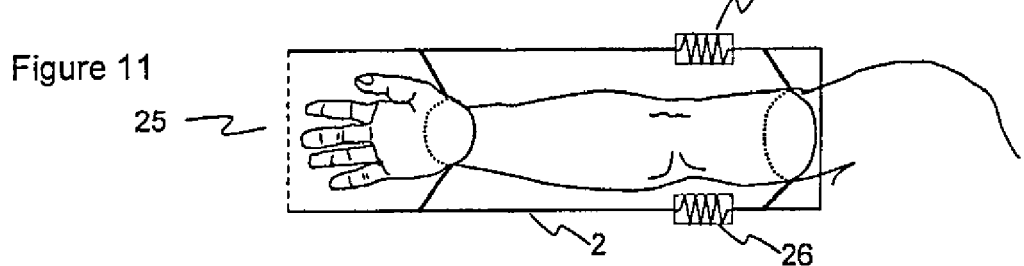

FIG. 11 illustrates the stage when the initially sealed end 3 has been opened by means of perforations 16 (illustrated in FIG. 10), leaving a now open end 25. In this state, the sleeve 2 will adopt a generally bunched configuration 26.

Figure 12:
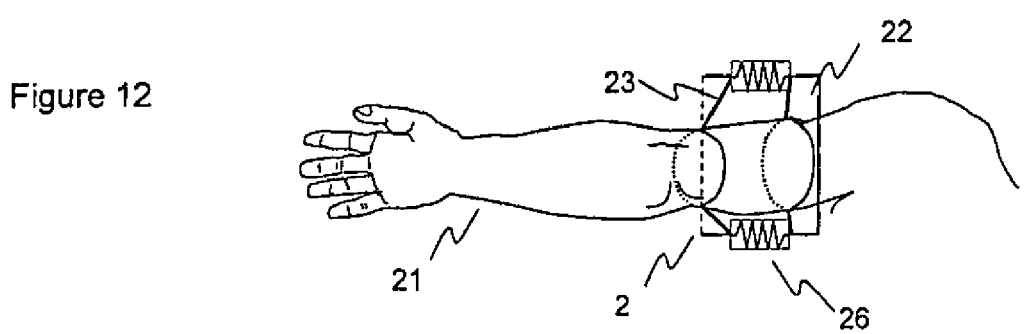

FIG. 12 illustrates the final situation where the sleeve 2 has been pulled up to the top of the arm 21, thus exposing the sterile skin ready for surgery. In this configuration, the sleeve 2 is in its bunched configuration 26 and the two limb-sealing means, 22 and 23, are close together. It is at this stage that the fastening means (not illustrated) are particularly useful in maintaining the sleeve 2 in this configuration. The wiping action of the limb-sealing means 23 when pulled from its position shown in FIG. 11 to that shown in FIG. 12 removes excess sterilising fluid from the surface of the arm 21.

The operation may now commence. At this stage, or after surgery, the whole device may be removed from the patient's arm by cutting and can be disposed with.

Figure 13A:
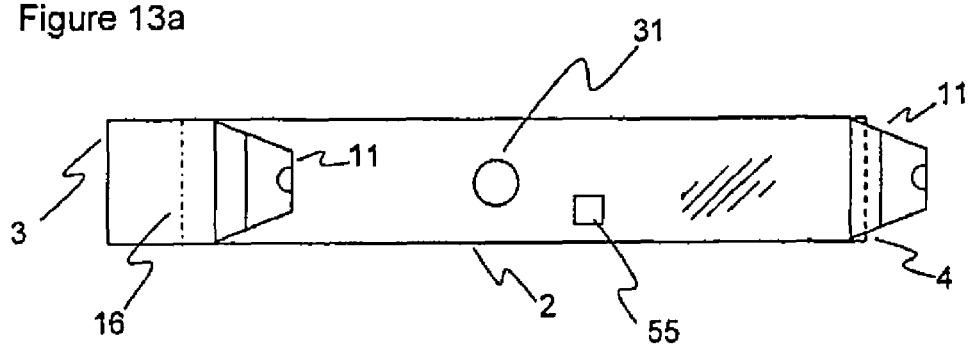
FIGS. 13a and 13b illustrate an embodiment of the invention with a port and means to absorb excess sterilising fluid.
Figure 13B:
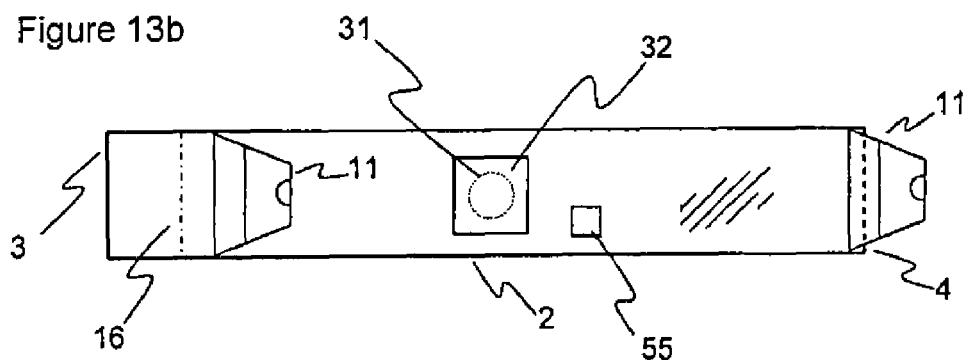

FIGS. 13a and 13b illustrate an embodiment of the invention wherein a port, or opening, 31 is provided in the tubular sleeve 2. The port 31 is sealed by the application of a suitable adhesive which is affixed to the sleeve 2 around the port 31 and to which a suitably shaped piece of waxed paper or other material 32 to which the adhesive will form a temporary and reversible bond is affixed. The port 31 thus provides a facility for the introduction of a liquid such as a sterilisation fluid or medicament (as appropriate) through the port, following the insertion of a user's limb into the limb sealing means 11 at the open end 4 of the sleeve 2. The combination of an appropriate adhesive and the waxed paper 32 allows the port 31 to be opened and re-sealed as required.

A block of suitable absorbent material as indicated by 55, such as sponge, may be included in the interior of the sleeve 2 to absorb any excess fluid (or other medicament) which remains once a user has spread the skin sterilisation fluid over a limb. Alternatively the skin sterilisation fluid may be provided in the form of a thixotropic agent which is initially a gel which becomes a liquid when spread on the patient's arm; the re-gelling of the agent then prevents unwanted flow of liquid.

Figure 14A:
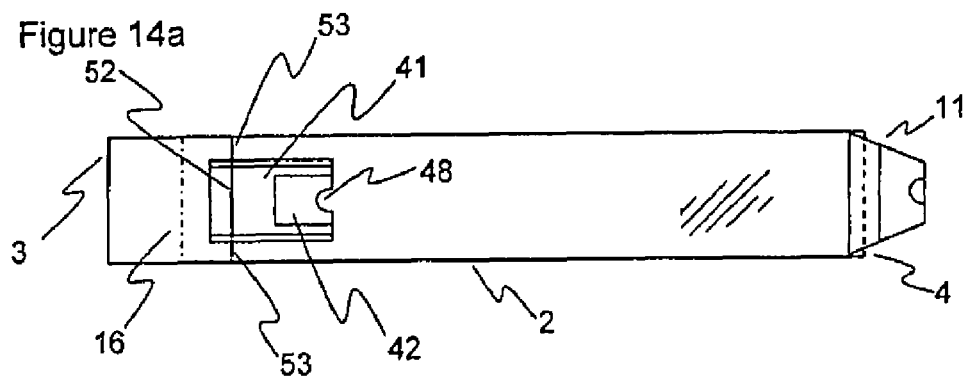
FIGS. 14a and 14b illustrate an embodiment of the invention incorporating a rectangular shaped limb sealing means.
Figure 14B:
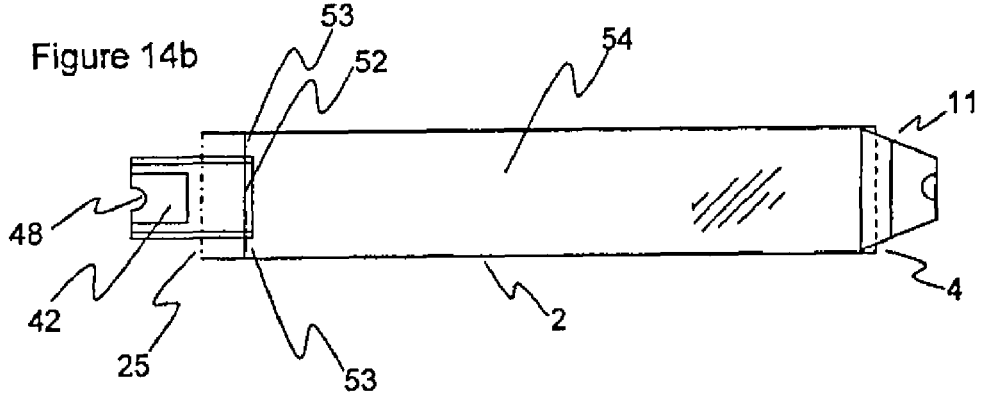

In another embodiment of the invention, the frustoconical member 12, as shown in FIG. 4, is replaced with a rectangular shaped member 41, as shown in FIGS. 14a and 14b, to which is attached a rectangular shaped limb sealing means 42 which incorporates a perforation/hole 48. The rectangular shaped member 41 is sized such that when a user inserts their hand or foot through the hole 48 in the limb sealing means 42, following the use of a sterilising solution within the sleeve 2 and removal of the sealed end 3 by means of the perforations 16, the user's hand or foot extends beyond the open end 25 of the sleeve 2. In this way, when the sleeve is pulled up to the top of the arm, contact between the unsterilised end 25 of the sleeve 2 and the sterilised arm is avoided.

Figure 15:
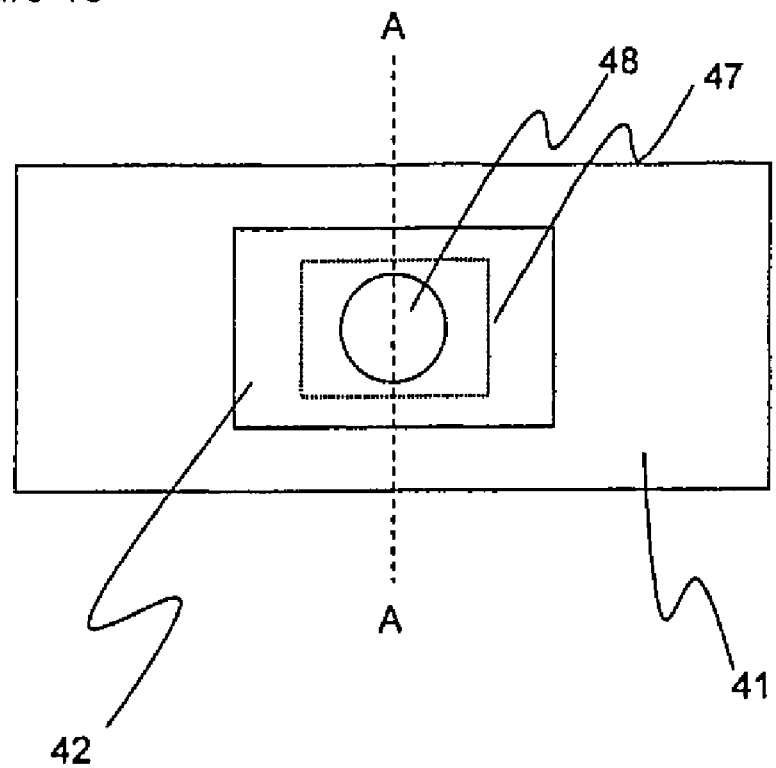
FIGS. 15 and 16 are schematic diagrams illustrating the construction of a rectangular, perforated, elastic diaphragm suitable for use as a limb-sealing means in combination with a rectangular shaped member used to attach the limb-sealing means to the inner surface of a sleeve.
Figure 16:
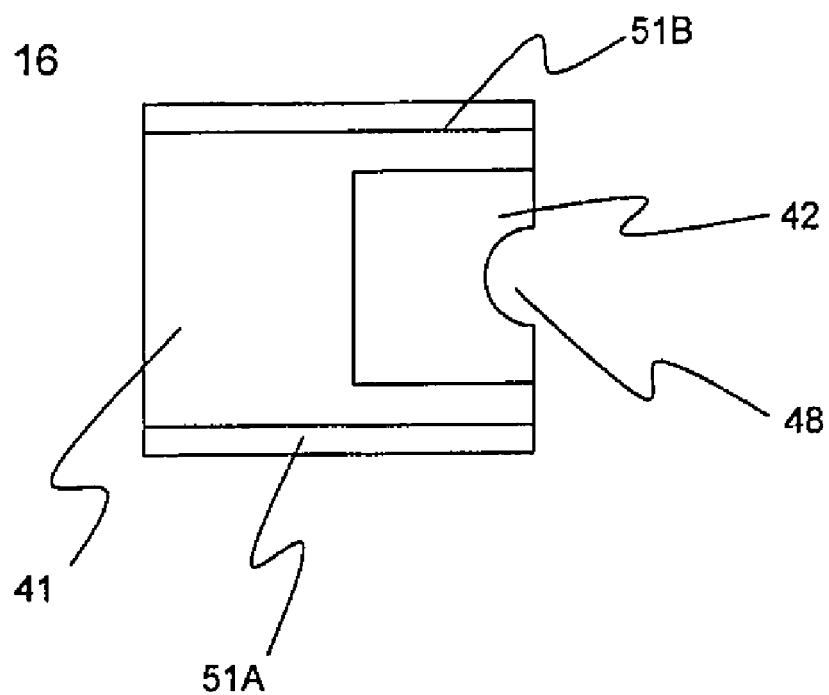

FIG. 15 illustrates the rectangular shaped member 41 and limb sealing means 42 prior to their insertion and attachment to the tubular sleeve 2. The rectangular shaped member 41 incorporates a central cut-out section indicated by the line 47. The limb sealing means 42 is attached to the member 41 by any suitable means such as heat welding, use of adhesive or double sided adhesive tape such that the hole 48 is aligned over the cut-out section. The rectangular shaped member 41 and attached limb sealing means 42 are initially folded along the line A-A to give the configuration shown in FIG. 16 and the adjacent faces of the member 41 are heat welded to each other along the lines 51A and 51B. The outer faces of the member 41 are then heat welded to the sleeve along the line 52 as indicated on FIGS. 14a and 14b such that the member 41 is located an appropriate distance from the location of the perforations 16. During this latter heat welding process the inner faces of the sleeve not separated by the member 41 are also welded to each other to form two seals 53. In use once a user's leg or hand has been inserted through the second limb sealing means 42 any liquid present in the main compartment 54 of the sleeve is retained there by the seals 53 in combination with the rectangular shaped member 41, the limb sealing means 42 and associated relevant seals.

Whereas the sleeve 2 of the present embodiment is produced from a transparent material the member 41 is preferably manufactured from a semi-opaque material, such that the member 41 and associated limb sealing means 42 can be easily distinguished from the sleeve 2 thus making it easier for the sleeve to be placed on the limb of a patient.

The limb sealing means 42 may be made of any suitable elastomeric material, although the thermoplastic rubber sold under the trade mark Kraton in sheet form has been found to be particularly suitable for this purpose. Kraton® is a polymer which while retaining elastic properties when stretched, does not rapidly return to its original shape. The material sold under the trade mark Elastoflex is also suitable. Thus when the limb sealing means 42 is stretched by a user inserting a limb, a seal is formed around the limb by the Kraton® but it is not a tight seal that would otherwise act as a tourniquet and so the limb sealing means provided adapt to fit limbs of differing circumference without the need to cut sections from the device.

The invention claimed is:

1. A device adapted to assist the sterilisation of a limb surface, and comprising:
    a flexible tubular sleeve having a proximal end and a distal end, the sleeve being closed at the distal end and being shaped and sized so as to have a circumference configured to loosely fit around the limb of a patient whose limb surface is to be sterilised; and
    respective elastic limb-sealing means radially inward of the flexible tubular sleeve, each located close to or at the respective ends of said sleeve, and each configured to form a seal between the sleeve and the limb of a patient,
    wherein the respective elastic limb-sealing means extend radially inwardly from the circumference of the tubular sleeve to form respective elastically deformable holes for forming the respective seals, the holes having an unstretched circumference substantially smaller than the circumference of the flexible tubular sleeve.

2. The device of claim 1 wherein at least one of the limb-sealing means comprises a perforated, elastic diaphragm.

3. The device of claim 1 wherein at least one of the limb-sealing means comprises a substantially frustoconical portion.

4. The device of claim 1 wherein the limb-sealing means are so constructed as to create a wiping action when slid, in use, along a patient's limb.

5. The device of claim 1 wherein both ends of the said sleeve are initially closed.

6. The device of claim 1 wherein the sleeve is substantially transparent.

7. The device of claim 1 wherein at least one of any sealed end of the sleeve is perforated, nicked, weakened, or otherwise adapted to assist opening of that sealed end.

8. The device of claim 1 further comprising at least one tab or loop to assist pulling the sleeve, in use, along a patient's limb.

9. The device of claim 1 further comprising one or more fasteners to hold the two ends of the sleeve close to each other, whilst the sleeve is positioned on a patient's limb.

10. The device of claim 1 with an easily rupturable container of sterilising agent inside the sleeve.

11. The device of claim 1 further comprising a valve arrangement to allow egress of air from within the sleeve whilst the sleeve is positioned on a patient's limb.

12. The device of claim 1 wherein at least one of the limb-sealing means is sized and shaped to be extendable beyond the respective end of the sleeve.

13. The device of claim 1 wherein at least one of the limb sealing means adapts to fit limbs of differing circumference without the need to cut sections from the device.

14. The device of claim 1 wherein a resealable portal is provided.

* * * * *